US010188476B1

(12) United States Patent
Jain et al.

(10) Patent No.: US 10,188,476 B1
(45) Date of Patent: Jan. 29, 2019

(54) MEDICAL GOWN HAVING AN INTEGRAL PROTECTIVE SLEEVE FOR MEDICAL EQUIPMENT

(71) Applicants: Sandeep Jain, Davie, FL (US); Saachi Jain, Davie, FL (US)

(72) Inventors: Sandeep Jain, Davie, FL (US); Saachi Jain, Davie, FL (US)

(*) Notice: Subject to any disclaimer, the term of this patent is extended or adjusted under 35 U.S.C. 154(b) by 197 days.

(21) Appl. No.: 15/250,490

(22) Filed: Aug. 29, 2016

Related U.S. Application Data

(60) Provisional application No. 62/315,657, filed on Mar. 30, 2016, provisional application No. 62/210,985, filed on Aug. 27, 2015.

(51) Int. Cl.
*A61B 46/10* (2016.01)
*A41D 13/12* (2006.01)
*A61B 7/02* (2006.01)

(52) U.S. Cl.
CPC .............. *A61B 46/10* (2016.02); *A41D 13/12* (2013.01); *A41D 13/1236* (2013.01); *A61B 7/02* (2013.01); *A41D 13/1209* (2013.01); *A41D 13/129* (2013.01); *A41D 13/1218* (2013.01); *A41D 13/1245* (2013.01); *A41D 13/1281* (2013.01)

(58) Field of Classification Search
CPC ...... A61B 46/10; A61B 7/02; A41D 13/1236; A41D 13/12; A41D 13/1209; A41D 13/1281; A41D 13/1245; A41D 13/1218; A41D 13/129
See application file for complete search history.

(56) References Cited

U.S. PATENT DOCUMENTS

| 5,033,115 | A | * | 7/1991 | Bowling | A41D 13/11 2/48 |
| 5,142,704 | A | * | 9/1992 | Viemeister | A41D 13/1218 2/171 |
| 5,414,867 | A | * | 5/1995 | Bowling | A41D 13/1209 2/114 |
| 5,548,842 | A | * | 8/1996 | Wiseman, Sr. | A41D 13/0002 128/201.29 |
| 6,186,957 | B1 | * | 2/2001 | Milam | A61B 7/02 600/528 |
| 6,317,894 | B1 | * | 11/2001 | Blechman | A41D 15/002 2/115 |
| 7,296,652 | B1 | | 11/2007 | Rosenberg | |

(Continued)

*Primary Examiner* — Khaled Annis
(74) *Attorney, Agent, or Firm* — Allen D.Hertz, P.A.; Allen D. Hertz

(57) ABSTRACT

A medical protective gown comprising a gown body. A centrally located orifice passes through a central region of a front panel of the gown body. A tubular protective sleeve extends forward from the front panel of the gown body, the tubular protective sleeve being located circumscribing the centrally located orifice. A tubular protective sleeve distal end panel is located at a distal end of the tubular protective sleeve. The tubular sleeve is adapted to receive a stethoscope or any other desired medical instrument. A broadened interior pocket is assembled to an interior surface of the gown body to support an upper, broader portion of the stethoscope or other instrument. A flange can be included with the tubular protective sleeve and/or the broadened interior pocket to aid in attachment to the gown body. The tubular protective sleeve can include a sleeve contraction system to contract the protective sleeve.

27 Claims, 9 Drawing Sheets

(56) References Cited

U.S. PATENT DOCUMENTS

| | | | |
|---|---|---|---|
| 7,575,094 B1 * | 8/2009 | Rosenberg | A45C 13/002 181/131 |
| 8,069,495 B2 | 12/2011 | Kemper | |
| 9,049,992 B2 | 6/2015 | Burmeister | |
| 2002/0170771 A1 * | 11/2002 | Milam | A61B 7/02 181/131 |
| 2009/0031474 A1 * | 2/2009 | Komorowski | A41D 13/0012 2/114 |
| 2009/0165186 A1 | 7/2009 | Mijares et al. | |
| 2015/0335470 A1 * | 11/2015 | Panser | A41D 13/0051 607/107 |

* cited by examiner

MEDICAL GOWN HAVING AN INTEGRAL PROTECTIVE SLEEVE FOR MEDICAL EQUIPMENT

CROSS REFERENCE TO RELATED APPLICATIONS

This is a United States Non-Provisional Utility Patent Application claims the benefit of:
U.S. Provisional Patent Application Ser. No. 62/315,657 filed on 30 Mar. 2016 (30 Mar. 2016), and
U.S. Provisional Patent Application Ser. No. 62/210,985 filed on 27 Aug. 2015 (27 Aug. 2015),
both of which are incorporated in their entireties herein by reference.
The one (1) year anniversary (Aug. 27, 2016) of the earliest Provisional Patent Application falls on a Saturday. Therefore, Applicant is afforded until the next business day (Monday, Aug. 29, 2016) to file the subject Non-Provisional Patent Application.

FIELD OF THE INVENTION

The present invention relates to a medical gown. More specifically, the present invention relates to a medical gown having an integral protective sleeve extending forward from an orifice located through a central region of a front panel of the gown and a broadened pocket extending upward from the orifice on an interior surface of the front panel of the gown.

BACKGROUND OF THE INVENTION

Medical professionals are exposed to a multitude of biohazardous conditions, including viruses, bacteria, and the like each workday. The medical profession utilizes a number of form factors of protective apparel and shields to protect themselves from exposure to the biomedical hazardous materials and contaminants. The protective apparel and shields would be respective to a specific level of anticipated conditions. For example, the medical professional would use gowns, masks, and gloves for general care. In more severe conditions, the medical professional would use enhanced protective gear, wherein the protective gear would completely cover the medical professional to ensure that "no skin is showing."

Protective apparel and shields are primarily directed towards protection of the medical professional to avoid direct transfer of biomedical hazardous materials. It is recognized that secondary transfer of biomedical hazardous materials and contaminants can cause equally hazardous exposure to the medical professional. For example, removal of the protective gear can transfer biomedical hazardous materials and contaminants from the exterior of the protective gear to the medical professional. In another example, the medical professional can be exposed to biomedical hazardous materials through subsequent contact with medical equipment used during diagnosis and/or treatment of the patient.

One exemplary medical device is a stethoscope. The stethoscope typically includes a small disc-shaped resonator that is placed against the patient, and two tubes connected to earpieces. Biomedical hazardous materials and contaminants can be transferred from the patient to any part of the stethoscope, including the resonator and/or the tubes. These undesirable biomedical hazardous materials would then be transferred to the medical professional or other person through secondary contact. The currently available equipment only considers use of the stethoscope in a free form, or more specifically independent of a protective medical gown. One known solution is to utilize a small protective cover, which is placed over the resonator. This solution has a number of limitations. One limitation would be the remaining exposed tubes. A second limitation is the requirement for removal of the protective cover, which introduces a potential for transfer of the contamination to the medical professional or other individual. The protective cover can continue to cause unwanted transfer of contaminations if the protective cover accidentally contacts another surface.

Accordingly, there remains a need in the art for a protective device and a method of use to minimize or eliminate any potential for transfer of contamination of biomedical hazardous materials from the patient to the medical professional(s).

SUMMARY OF THE INVENTION

The present invention overcomes the deficiencies of the known art by disclosing an apparatus and a method for providing personal protection for a medical professional, including a protective gown, wherein the protective gown introduces a system for protecting a stethoscope from exposure to contaminants, such as biomedical hazardous materials.

In accordance with one embodiment of the present invention, the invention consists of a protective gown comprising:
 a gown body adapted to be worn by a medical professional, the gown body defining a front panel having an exterior surface and an interior surface;
 an orifice centrally located in a central region of a front panel of the gown; and
 a tubular protective sleeve extending forward from the gown body circumscribing the centrally located orifice; and
 wherein the gown body and tubular protective sleeve are fabricated of a material and assembled to one another creating an impervious barrier to biomedical hazardous materials.

In a second aspect, centrally located orifice is designed having a diameter adapted to enable passage of a disc-shaped resonator of a stethoscope.

In another aspect, the tubular protective sleeve is designed having a diameter adapted to receive the disc-shaped resonator of the stethoscope.

In yet another aspect, the tubular protective sleeve comprises a tubular structure terminating at a sealed distal end.

In yet another aspect, the sealed distal end is formed using a panel contiguously joined to a circumferential edge of a tubular protective sleeve body.

In yet another aspect, the sealed distal end is formed using a panel formed from a portion of the tubular section, folded, and contiguously joined to a circumferential edge of a tubular protective sleeve body.

In yet another aspect, a flange is formed or joined to a proximal end of the tubular protective sleeve body, wherein the flange is adapted for contiguously joining the tubular protective sleeve body and the gown body with one another.

In yet another aspect, the gown body can be fabricated with the interior surface being of a first color and the exterior surface being of a second color, wherein the first color and the second color are different from one another. The color differentiation is provided to aid the user in ensuring the user only contacts safe, interior surfaces when removing a contaminated gown body.

In yet another aspect, the gown body can include one or more pockets. The pockets can be fabricated of a clear material enabling the user to view an article or articles carried within the pocket. This would enable viewing of a cellular phone, pager, tablet, a clock, or any other device being carrier therein.

In yet another aspect, the gown body can include a mask. The mask can be joined to the gown body using any suitable joining technique. In one configuration, the joint formed between the mask and the gown body would be contiguous providing a seam that is impervious to biomedical hazardous materials.

In yet another aspect, the gown body can include a pair of gloves. The pair of gloves can be joined to the gown body using any suitable joining technique. In one configuration, the joint formed between the each glove and the gown body would be contiguous providing a seam that is impervious to biomedical hazardous materials.

In yet another aspect, the gloves can be fabricated from the gown body, thus being integrally and unitarily formed therewith.

In yet another aspect, the gown body can include one or more mechanical couplers, such as snaps, ties, dense hook and loop tape, and the like to support a weight of any carried medical equipment, personal equipment (such as a cellular phone, a portable phone, a recording device, etc.), and the like.

In yet another aspect, the gown body can include one or more reinforcing members to support a weight of any carried medical equipment, personal equipment (such as a cellular phone, a portable phone, a recording device, etc.), and the like.

In yet another aspect, the gown body and the tubular protective sleeve are fabricated of the same material.

In yet another aspect, the gown body and the tubular protective sleeve are fabricated of different materials.

In yet another aspect, the tubular protective sleeve is fabricated of a clear or translucent material.

In yet another aspect, a broadened interior pocket extending upward from the centrally located orifice on an interior surface of the front panel of the gown.

In yet another aspect, a broadened interior pocket is formed having a broader upper opening than a lower base section.

In yet another aspect, the broadened interior pocket is formed having a conical or funnel shape.

In yet another aspect, the broadened interior pocket is formed having a semi-circular shape.

In yet another aspect, the broadened interior pocket is formed having a "U" shape.

In yet another aspect, the broadened interior pocket is formed having a "V" shape.

In yet another aspect, a broadened interior pocket is formed having a rectangular shape.

In yet another aspect, the broadened interior pocket further includes a broadened interior pocket stethoscope lead in.

In yet another aspect, a broadened interior pocket is symmetrically shaped about the centrally located orifice.

In yet another aspect, a broadened interior pocket is symmetrically shaped about an elongated, longitudinal axis extending through a center of the centrally located orifice.

In yet another aspect, the gown would additionally include extra material provided adjacent to the neckline. The extra material provides the user with a means for gripping portions of the medical equipment (stethoscope, etc.) during use and removal.

In yet another aspect, the distal end of the tubular protective sleeve can be bulbous.

In yet another aspect, elastic or any other element can be integrated into the distal end of the protective sleeve to gather the end, tightening the material over the acoustic surface of the resonator.

In yet another aspect, the gown can be shaped to include excess material proximate the neckline, wherein the excess material provides a gripping surface for the medical professional to grip the earpieces of the stethoscope.

In yet another aspect, the excess material for gripping the earpieces of the stethoscope can be provided in a form of a pocket, wherein the opening of the pocket would be located in an upper region of the protective gown body/torso section.

In yet another aspect, the stethoscope adjustment pocket(s) can be formed extending inward into the broadened interior pocket.

In yet another aspect, the tubular protective sleeve can be adapted to accommodate a wireless, two unit stethoscope, such as a Bluetooth stethoscope.

In yet another aspect, the tubular protective sleeve can be adapted to accommodate other medical equipment, such as a hand held ultrasound device, and any other portable medical equipment and/or remote medical hand piece.

In use, the disc-shaped resonator and the associated tubular portion of the stethoscope is inserted into the tubular protective sleeve from the interior side of the gown body. The broader section of the stethoscope comprising the pair of tubes and the associated earpieces reside within the broadened pocket. The medical professional would guide the resonator to the distal end of the tubular protective sleeve and utilize the stethoscope in accordance with common practice. The distinction is that the stethoscope resides within a protective barrier during use.

In yet another aspect, the tubular protective sleeve can further include a sleeve contraction system.

In yet another aspect, the tubular protective sleeve contraction system comprises at least one sleeve contracting mechanism.

In yet another aspect, each at least one sleeve contracting mechanism is a flexible elongated draw element.

In yet another aspect, the flexible elongated draw element is at least one of a string, a rope, a cord, a flexible piece of twine, a ribbon, a flexible elongated plastic element, monofilament, a strip of fabric, flexible wire, flexible insulated wire, and the like.

In yet another aspect, the tubular protective sleeve contraction system comprises at least one flexible elongated draw element extending through a series of spatially arranged draw element guide loops.

In yet another aspect, the tubular protective sleeve contraction system comprises a plurality of flexible elongated draw elements, each flexible elongated draw element extending through a respective series of spatially arranged draw element guide loops.

In yet another aspect, the series of spatially arranged draw element guide loops is located on an interior surface of the tubular protective sleeve.

In yet another aspect, the at least one flexible elongated draw element is routed through an eyelet located through the broadened interior pocket.

In yet another aspect, the tubular protective sleeve can be retained against an exterior surface of the gown body by a tubular protective sleeve retention member.

In yet another aspect, the tubular protective sleeve retention member can include a mechanical fastener. The mechanical fastener can include snaps, a tie, a ribbon, a pocket, magnets, and the like.

In yet another aspect, the tubular protective sleeve retention member can include a pair of mating dense hook and loop tape sections.

In yet another aspect, the tubular protective sleeve retention member can include a pocket.

These and other aspects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, in which.

Like reference numerals refer to like parts throughout the several views of the drawings.

DETAILED DESCRIPTION OF THE PRESENT INVENTION

Detailed embodiments of the present invention are disclosed herein. It will be understood that the disclosed embodiments are merely exemplary of the invention that may be embodied in various and alternative forms. The figures are not necessarily to scale, and some features may be exaggerated or minimized to show details of particular embodiments, features, or elements. Specific structural and functional details, dimensions, or shapes disclosed herein are not limiting but serve as a basis for the claims and for teaching a person of ordinary skill in the art the described and claimed features of embodiments of the present invention. The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims.

Figure 1:
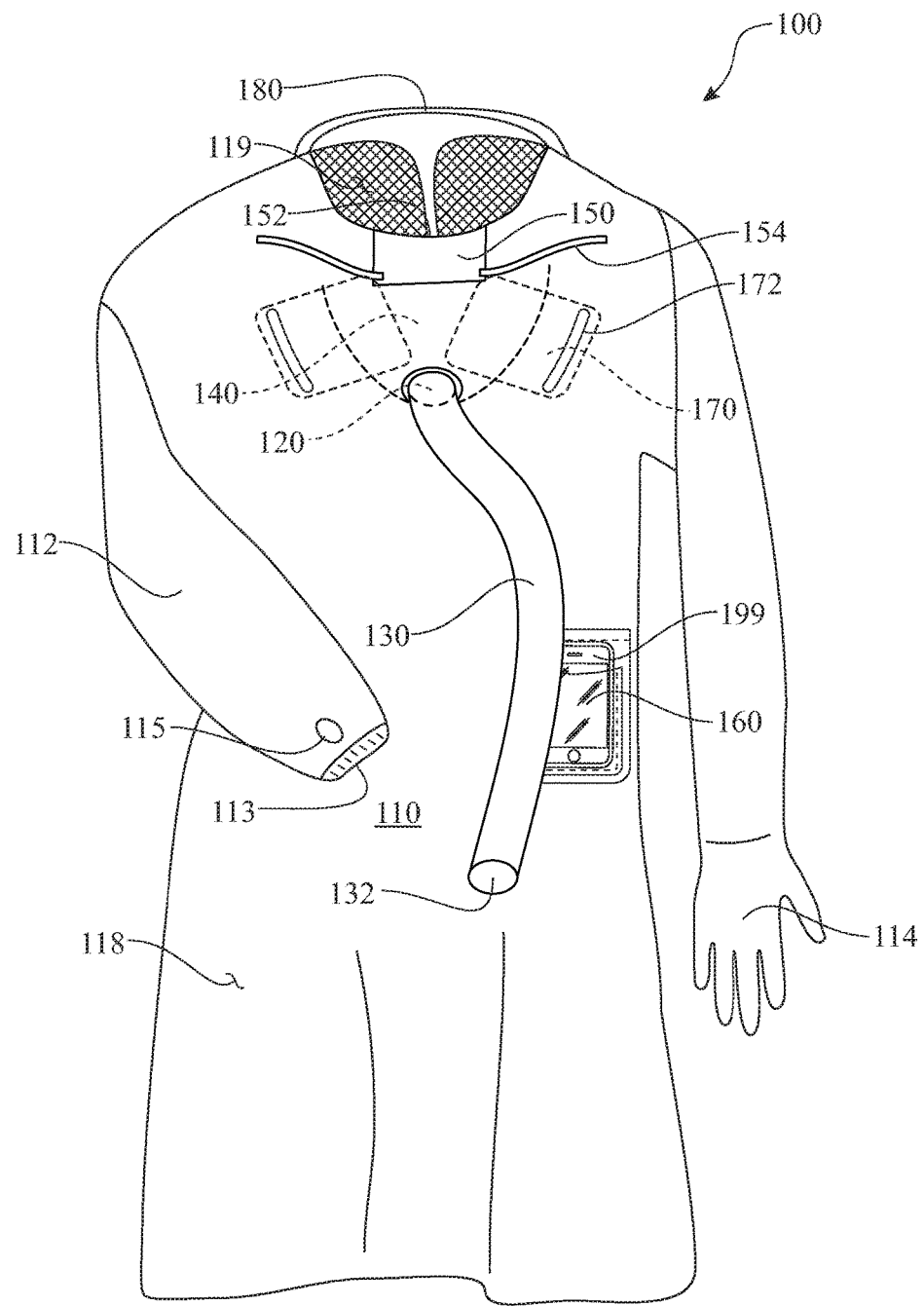
FIG. 1 presents a front plan view of an exemplary protective gown having a gown body and protective tubular sleeve extending forward from the gown body circumscribing a centrally located orifice.

For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

A protective gown 100 is fabricated by shaping a raw material into a protective gown body 110, as illustrated in FIGS. 1 through 6. The protective gown body 110 is defined having an exterior surface 118 (illustrated in FIG. 1) and an interior surface 119 (illustrated in FIG. 2). The protective gown body 110 is shaped to include features adapting the protective gown 100 to be worn by a medical professional during examination and/or treatment of a patient. The protective gown body 110 can be fabricated of a reusable or disposable material. The features include a torso covering section, a neckline (formed as either an aperture or a wrapped edge) provided at an upper end of the torso section, and a pair of sleeves 112, each protective gown sleeve 112 extending outward from a respective side of the torso section (main body). The protective gown 100 can include an optional securing mechanism, such as a waistband tie (as shown), snaps, a zipper, a dense hook and loop tape, and the like. The protective gown body 110 can include a finger loop 115 located at a distal end of each protective gown sleeve 112 to aid in retaining the protective gown sleeve 112 in an extended position when worn. The finger loop 115 would be created by forming an aperture through the protective gown sleeve 112 proximate a distal end thereof, such as those best shown in FIG. 2.

The interior surface 119 of the protective gown body 110 can be of a first color. The exterior surface 118 of the protective gown body 110 can be of a second color. Wherein the first color and the second color are different from one another. The color distinctions would aid in a safe removal of the protective gown 100 from the medical professional, wherein the interior can be contacted and one would avoid contact with the contaminated exterior surface.

Figure 2:
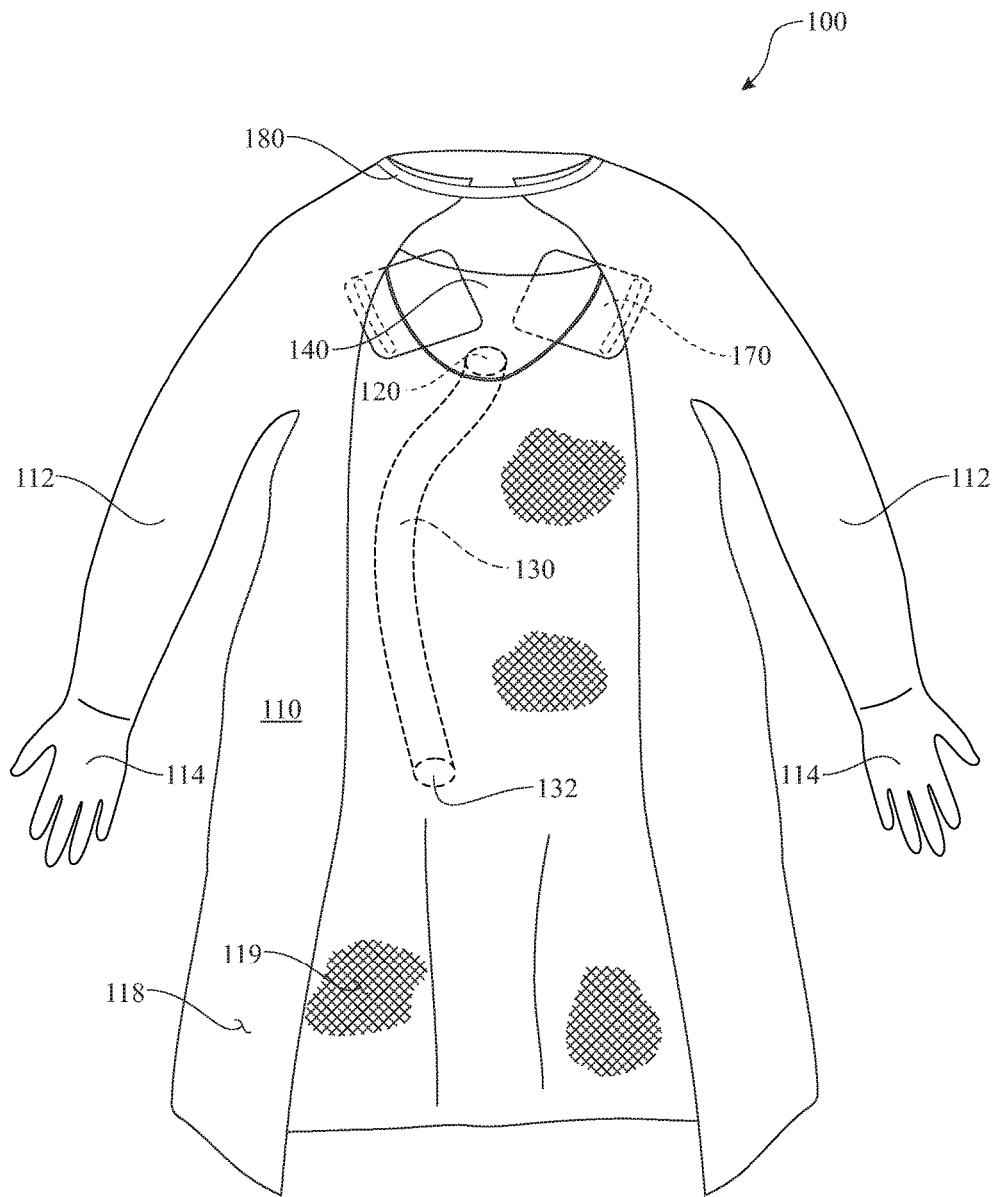
FIG. 2 presents a rear plan view of the exemplary protective gown introducing a broadened pocket.
Figure 3:
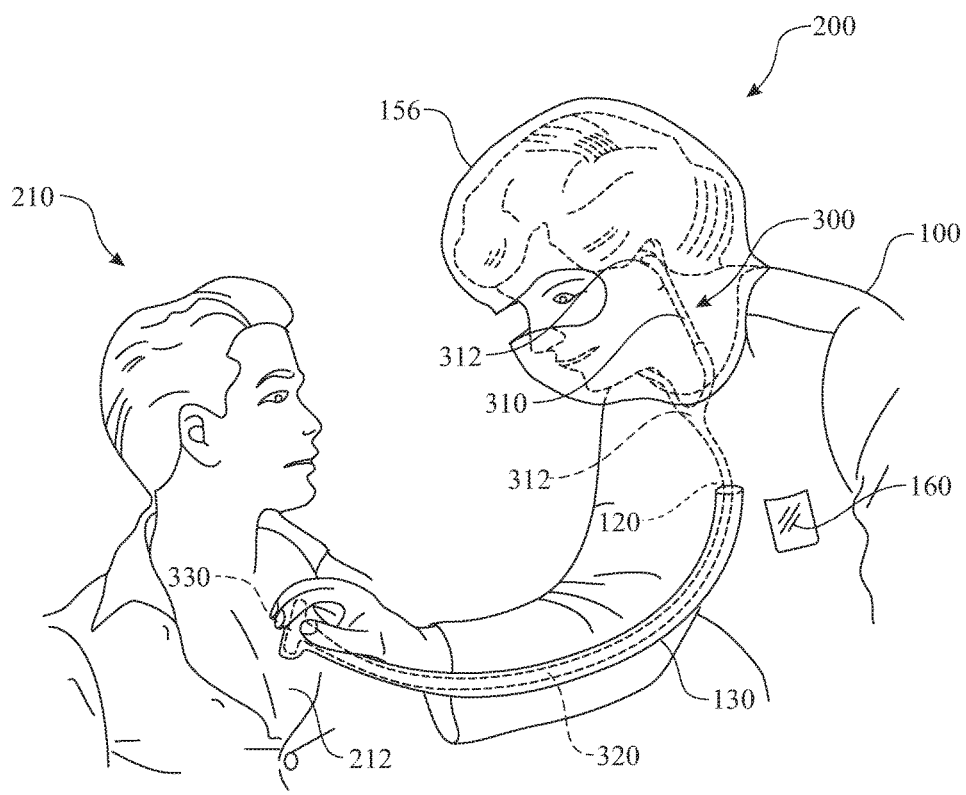
FIG. 3 presents an exemplary perspective view of a medical professional attending to a patient, wherein the medical professional is wearing and using the protective gown.

The exemplary protective gown 100, introduced in an exterior, front view presented in FIG. 1 and in an interior, rear view presented in FIG. 2, is adapted to receive a stethoscope 300, illustrated in use in FIG. 3, in a manner to provide a barrier between the stethoscope 300 and any undesirable biomedical hazardous materials. The stethoscope 300 is an acoustic medical device for auscultation, or listening to the internal sounds of an animal or human body. The stethoscope 300 is a medical instrument for listening to the action of someone's heart or breathing, typically having a small disc-shaped resonator 330 that is placed against a chest 212 of a patient 210, and two tubes 320, 322 connected to earpieces 310, 312.

A centrally located orifice 120 is cut through a centrally located region of the protective gown body 110. The centrally located orifice 120 would be located at a position optimal for receiving a transition point between the flexible tubing 320 and the stethoscope bisected tubing section 322 of the stethoscope 300. The centrally located orifice 120 would preferably have a diameter and shape adapted to enable the disc-shaped resonator 330 located at a distal end of the stethoscope 300 to pass therethrough. A proximal end of the tubular protective sleeve 130 is contiguously joined to the protective gown body 110 about the centrally located orifice 120. The attachment can be accomplished by including a flange about the proximal end of the tubular protective sleeve 130. The flange can be located on an interior side of the protective gown body 110 or an exterior side of the protective gown body 110. The assembly can include a pair of flanges, placing one on the interior side of the protective gown body 110 and the other on the exterior side of the protective gown body 110. A tubular protective sleeve distal end panel 132 can be contiguously assembled to a distal end of the tubular protective sleeve 130, wherein the tubular protective sleeve distal end panel 132 provides a planar surface for placement between a functional surface of the disc-shaped resonator and the patient.

The protective gown body 110, the tubular protective sleeve 130, and the tubular protective sleeve distal end panel 132 can be fabricated of the same material or different materials. The tubular protective sleeve 130 and/or tubular protective sleeve distal end panel 132 can be fabricated of an opaque material, a translucent material, or a transparent material. The tubular protective sleeve 130 is preferably designed having a diameter adapted to receive and enable passage of the disc-shaped resonator. The size and shape of the tubular protective sleeve distal end panel 132 would be sufficient to cover the operational surface of the disc-shaped resonator, while ensuring against any degradation in functionality thereof.

A broadened interior pocket 140 can be provided on an interior surface of the protective gown body 110. The broadened interior pocket 140 would be shaped to receive the broader portion or stethoscope bisected tubing section 322 of the stethoscope 300, wherein the stethoscope bisected tubing section 322 of the stethoscope 300 includes the pair of tubes and a pair of stethoscope binaurals 310, each stethoscope binaural 310 having a respective stethoscope earpiece 312. The broadened interior pocket 140 can be provided in a semi-circular shape, a "V" or triangular shape ("V" shaped broadened interior pocket 142), a "U" shape ("U" shaped broadened interior pocket 144), a rectangular shape (rectangular shaped broadened interior pocket 146), or any other suitable shape (elliptical, oblong, quadrilateral, pentagonal, hexagonal, octagonal, and the like). The broadened interior pocket 140 would be sized to retain the upper portion of the stethoscope 300 in position, ready for use when needed. The stethoscope binaurals 310 would be seated within the broadened interior pocket 140, thus being protected by the protective gown 100 when not in use. The broadened interior pocket 140 can be fabricated from the same material as the protective gown body 110 or of a different material. A lower portion of the broadened interior pocket 140 would be preferably located below the centrally located orifice 120.

The distal end of the tubular protective sleeve 130 can incorporate any of a number of features to enhance the use thereof. For example, the distal end of the tubular protective sleeve 130 can be formed having a bulbous shape to accommodate an operational orientation of the disc-shaped resonator. In a second example, a gathering element can be integrated into the distal end of the tubular protective sleeve 130, wherein the gathering element would pull the tubular protective sleeve distal end panel 132 taught over the operational surface of the disc-shaped resonator. The gathering element can be any suitable component capable of gathering or collecting any excess material, such as elastic, a ribbon or other tie, snaps, dense hook and loop tape, and the like.

Another exemplary additional feature is an inclusion of excess material proximate a neckline of the protective gown body 110. The excess material provides a section of material where the medical professional can grip each stethoscope binaural 310 of the stethoscope 300 without direct contact. The excess material is representative of any suitable configuration of material enabling the desired result. The excess material can be formed as an oversized collar, a pocket 170, a lapel, or any other suitable shape.

Figure 7:
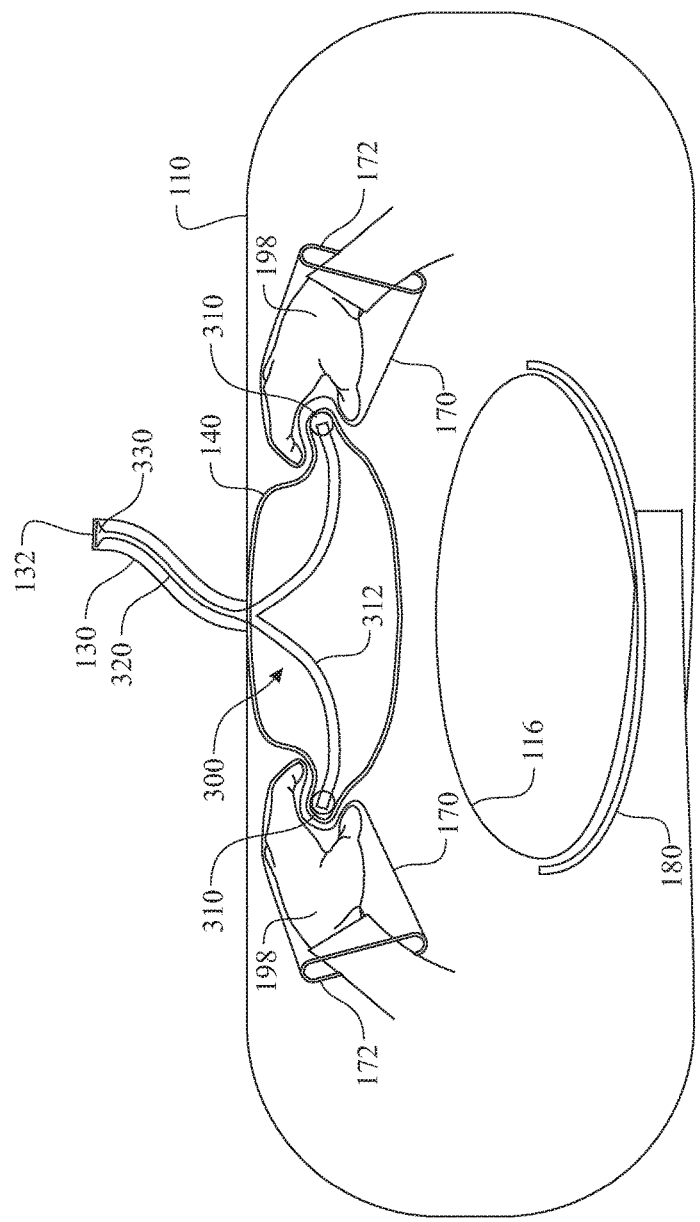
FIG. 7 presents a top schematic view illustrating how a medical professional can employ a pair of adjustment access pockets to grip and position a medical device, such as a stethoscope binaural.

When configured as a pocket 170, the pocket 170 could be fabricated of independent sheets of material and contiguously joined to the protective gown body 110. A pocket aperture 172 would be cut through the protective gown body 110. The pocket 170 would be located about the aperture 172. An edge of the pocket 170 circumscribing an opening edge of the pocket would be joined to the protective gown body 110 about the aperture 172. The joint can be formed on an interior and/or an exterior of the protective gown body 110 maintaining an adequate barrier between any potential contamination and the medical professional. The stethoscope adjustment access pocket 170 is preferably configured enabling the user to grip the stethoscope binaural 310, as illustrated in FIG. 7. The user would insert each glove covered hand 198 through the pocket aperture 172, into each respective stethoscope adjustment access pocket 170. The user would then locate and grip each respective stethoscope binaural 310 of the stethoscope 300. The glove provides one barrier. The stethoscope adjustment access pocket 170 provides a second barrier. And when applicable, the broadened interior pocket 140 provides a third barrier. The user can grip the stethoscope binaural 310 at a location where the stethoscope binaural 310 is covered by the broadened interior pocket 140 or at a location above the broadened interior pocket 140, where the stethoscope binaural 310 is free or extending above an upper edge of the broadened interior pocket 140. The configuration enables use of the stethoscope 300 while ensuring against any exposure to contamination thereof. The user can place the earpieces in the user's ears as desired and return the stethoscope 300 to a stored position exclusive of direct contact.

Another exemplary additional feature is an attached mask 150. The attached mask 150 would be attached to the protective gown body 110 in any suitable configuration. In the exemplary configuration, the attached mask 150 is joined to the protective gown body 110 by a mask and gown seam 152. The mask and gown seam 152 provides a seam that is impervious to biomedical hazardous materials. It is understood that the mask 150 can be shaped from a section of material used for shaping the protective gown body 110, thus being integral and unitarily formed therewith. The mask can include one or more mask retention straps 154 for securing the mask 150 in position on the medical professional.

The attached mask 150 is one exemplary facial covering. It is understood that the facial or head covering 150, 156 can be a partial head covering 156 attached to the gown body 110 at a location proximate a neckline of the gown body 110, or a complete head covering 156 attached to the gown body 110 at a location proximate a neckline of the gown body 110, as shown in FIG. 3.

Another exemplary additional feature is an inclusion of a pair of gloves 114 attached and/or integral with the protective gown body 110. Each glove 114 would be joined to the distal end of the protective gown sleeve 112 of the protective gown body 110 using a seam or other joint that is impervious to biomedical hazardous materials. In an alternative configuration, the gloves 114 can be shaped from the section of material used for shaping the protective gown sleeve 112.

In another variant, an end of each protective gown sleeve 112 can include a gathered sleeve opening 113, as shown in FIG. 1. The gathered sleeve opening 113 is designed to gather the end of the protective gown sleeve 112 securely about a wrist of the medical professional wearing the protective gown 100. A finger loop 115 can be formed through the protective gown sleeve 112 at a location proximate the gathered sleeve opening 113, wherein the medical professional would insert one of their fingers through the finger loop 115, wherein worn this way, the finger retains the protective gown sleeve 112 from walking up the arm of the medical professional.

In an alternative configuration, the tubular protective sleeve 130 and broadened interior pocket 140 can be assembled to one another. The tubular protective sleeve 130 would be inserted through centrally located orifice 120. A portion of either or both of the tubular protective sleeve 130 and the broadened interior pocket 140 can be used as a flange for attachment of the assembly to the protective gown body 110. Based upon the shape of the broadened interior pocket 140, it would be preferred to secure the attachment flange to the interior surface of the protective gown body 110. It is understood that the seam between the flange and the protective gown body 110 can be sealed to minimize collection of any contaminants. A second flange can be provided on the tubular protective sleeve 130, wherein the first flange (integral with the broadened interior pocket 140) and the second flange (on the tubular protective sleeve 130) can sandwich the protective gown body 110 therebetween, thus further optimizing the sealing boundary.

It is critical to ensure that the interior of the protective gown 100 remains free of any contamination. A temporary support strap 180 can be included on the protective gown 100 at a location proximate a neckline thereof. The temporary support strap 180 would be used by the medical professional 200 to aid the medical professional 200 during a process of placing the protective gown 100 onto their body.

Figure 5:
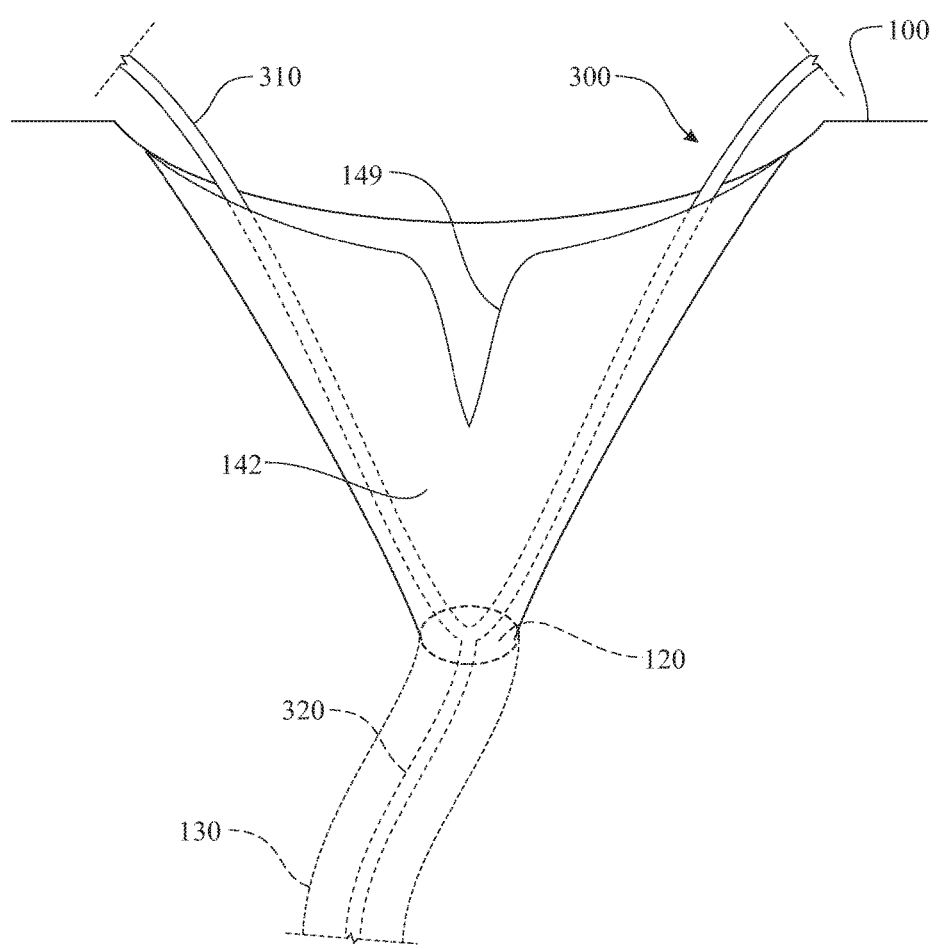
FIG. 5 presents an enlarged rear plan view of a first exemplary broadened interior pocket, the first exemplary broadened interior pocket being provided in a "V" shape.
Figure 6:
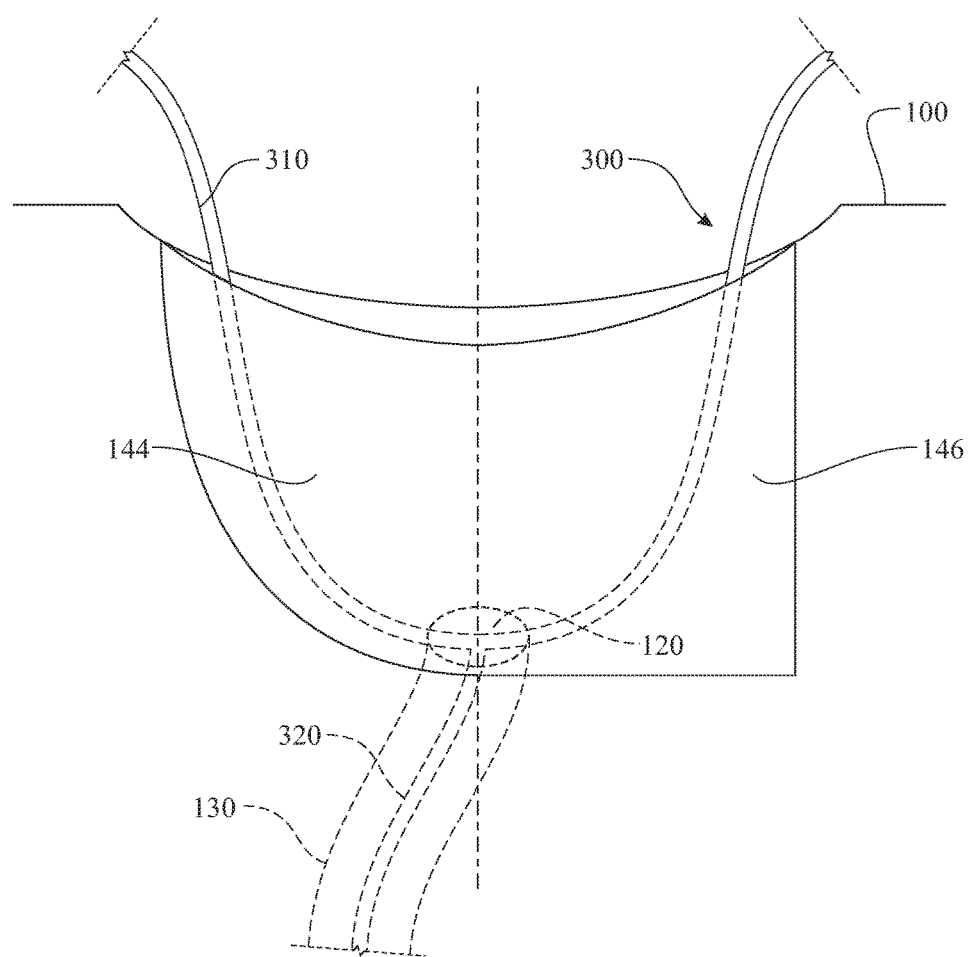
FIG. 6 presents an enlarged rear plan view of two additional exemplary broadened interior pockets, one side being exemplary of a broadened interior pocket being provided in a "U" shape and the second side being exemplary of a broadened interior pocket being provided in a rectangular shape.

An example of the protective gown 100 in use is presented in FIG. 3. A medical professional 200 would wear the protective gown 100 during an examination of a patient 210. A stethoscope 300 would be placed into the protective gown 100 by inserting a drum and diaphragm 330 and an associated flexible tubing 320 of the stethoscope 300 through the centrally located orifice 120 and feeding the drum and diaphragm 330 down through the tubular protective sleeve 130 until seated against an interior surface of the tubular protective sleeve distal end panel 132. When the tubular protective sleeve 130 is seated against the interior surface of the tubular protective sleeve distal end panel 132, a stethoscope bisected tubing section 322 of the stethoscope 300 would be seated into the broadened interior pocket 140 (as best shown in FIGS. 5 and 6). Stethoscope binaurals 310 would extend upward from the broadened interior pocket 140 and be arranged enabling ease of insertion of each earpiece 312 into a respective ear of the medical professional 200. One or more mechanical fasteners (not shown) can be included to secure an upper free edge of the broadened interior pocket 140 to the respective surface of the protective gown body 110, securing the stethoscope bisected tubing section 322 in position. The mechanical fasteners can be of any suitable format, including a dense hook and loop tape, a snap, a button, a tie, and the like.

The medical professional 200 would place the temporary support strap 180 about their neck. The temporary support strap 180 would retain the protective gown 100 upon their body while they slip their each arm into each respective protective gown sleeve 112. This is particularly helpful if the stethoscope 300 was previously placed within the protective gown 100.

The protective gown 100 can include a stethoscope adjustment access pocket 170, wherein the stethoscope adjustment access pocket 170 provides a workable barrier between an exposed glove worn by the medical professional 200 and the stethoscope binaural 310 of the stethoscope 300 to ensure against transfer of any contamination between exposed gloves worn by the medical professional 200 and the stethoscope binaural 310. The stethoscope adjustment access pocket 170 would be integral with the protective gown 100 providing an adequate contamination barrier. The pocket aperture 172 provides access to an interior of the stethoscope adjustment access pocket 170, while maintaining the adequate contamination barrier. This configuration would be adaptable to a common gown 100, a complete body protection suit, or any other protective gown configuration.

The broadened interior pocket 140 can be provided in any suitable shape. Several exemplary shaped broadened interior pockets 140 are illustrated in FIGS. 5 and 6. In one variant, the broadened interior pocket 140 can be provided in a "V" shape, identified as a "V" shaped broadened interior pocket 142, shown in FIG. 5. An exemplary broadened interior pocket stethoscope lead in 149 is formed along an opening edge of the "V" shaped broadened interior pocket 142, wherein the broadened interior pocket stethoscope lead in 149 is provided to aid the user during a process of inserting the stethoscope 300 into the "V" shaped broadened interior pocket 142 and guiding the flexible tubing 320 into the tubular protective sleeve 130. In a second variant, the broadened interior pocket 140 can be provided in a "U" shape, identified as a "U" shaped broadened interior pocket 144, shown on a left side of the example illustrated in FIG. 6. In a third variant, the broadened interior pocket 140 can be provided in a rectangular shape, identified as a rectangular shaped broadened interior pocket 146, shown on a right side of the example illustrated in FIG. 6.

Figure 8:
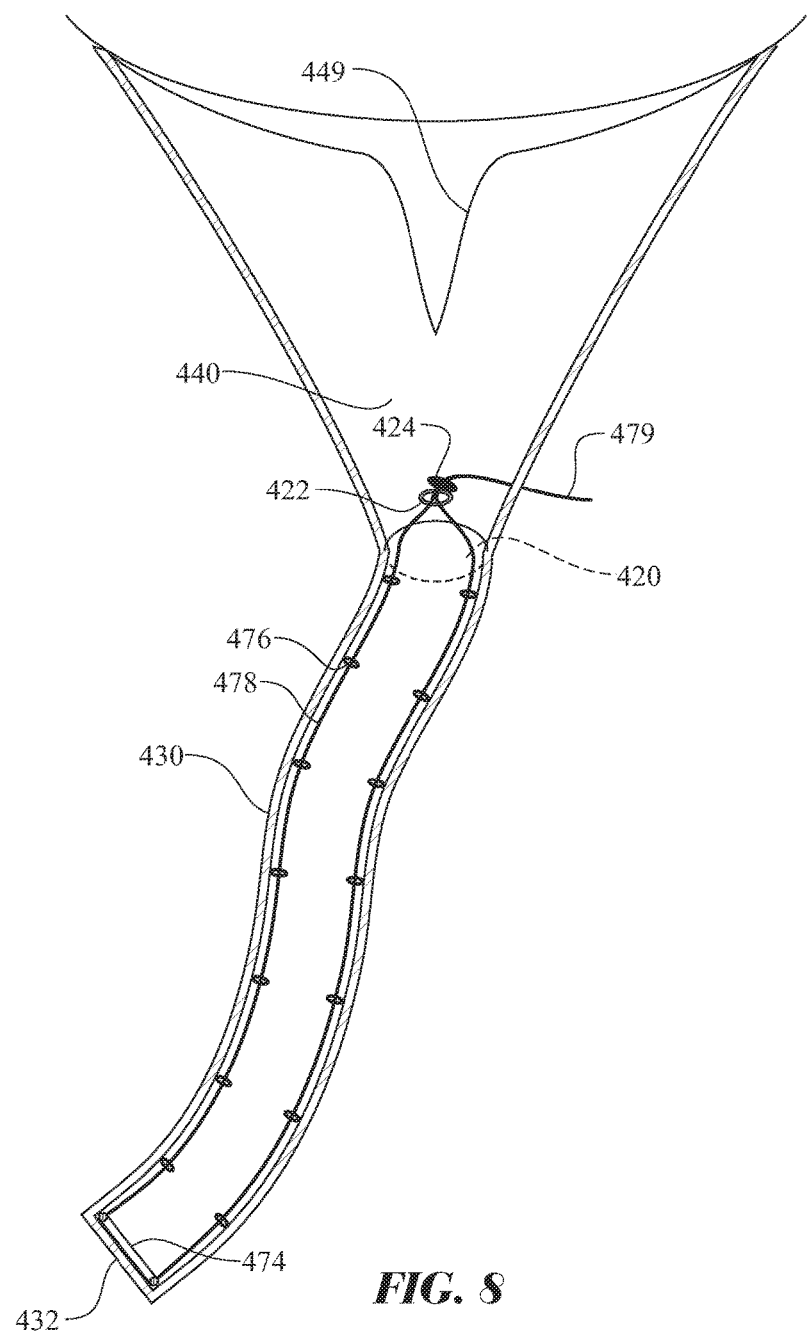
FIG. 8 presents a sectioned elevation rear view of an exemplary enhanced tubular protective sleeve, wherein the tubular protective sleeve includes a sleeve contraction system, the tubular protective sleeve being shown in an expanded condition.

The protective gown 100, more specifically, the tubular protective sleeve 130 can be enhanced, as illustrated in FIG. 8. A tubular protective sleeve 430 is an enhanced version of the tubular protective sleeve 130. Like features of the tubular protective sleeve 430 and the tubular protective sleeve 130 are numbered the same except preceded by the numeral '4'. The tubular protective sleeve 430 introduces a sleeve contraction system. The sleeve contraction system can employ any suitable contraction system configuration. The exemplary embodiment comprises a series of draw element guide loops 476. The draw element guide loops 476 are carried by an interior surface of the tubular protective sleeve 430. The draw element guide loops 476 are preferably configured in a linear, spatial arrangement along a line parallel to an elongated axis of the tubular protective sleeve 430. A draw element 478 is routed through each series of draw element guide loops 476. A distal end of each draw element 478 is secured to a tubular protective sleeve distal end panel 432 of the tubular protective sleeve 430 and a grip or free end of the draw element 478 is routed through draw element collection guide eyelet 422, wherein the draw element collection guide eyelet 422 is assembled to a broadened interior pocket 440. A draw element grip end retention element 424 can be secured to the grip or free end of the draw element 478 to ensure the grip or free end of the draw element 478 does not slip towards the tubular protective sleeve distal end panel 432. The draw element grip end retention element 424 can be adapted to collect and retain each of the at least one draw element 478, referred to as a collective draw elements 479. An optional distal end panel support element 474 can be located a distal end of the tubular protective sleeve 430, proximate the tubular protective sleeve distal end panel 432. The distal end panel support element 474 would be sized, shaped, and of a material to avoid interference with the drum and diaphragm 330 of the stethoscope 300. In one exemplary configuration, the distal end panel support element 474 would be of a ring shaped plastic. The distal end of each draw element 478 would be secured to the distal end panel support element 474.

In use, the medical professional would insert the drum and diaphragm 330 of the stethoscope 300 through the tubular protective sleeve 430 and into the distal end of the tubular protective sleeve 430, proximate the tubular protective sleeve distal end panel 432. The medical professional would then grip the drum and diaphragm 330 through the tubular protective sleeve distal end panel 432 and draw the tubular protective sleeve 430 outward or downward, drawing the flexible tubing 320 into the tubular protective sleeve 430 until the tubular protective sleeve 430 is completely extended. A grip assisting feature, such as a loop, a string, and the like, can be provided on an exterior surface of the tubular protective sleeve distal end panel 432, wherein the grip assisting feature provides a grip to assist the user in drawing the tubular protective sleeve 430 into the extended configuration, as illustrated in FIG. 8.

Figure 9:
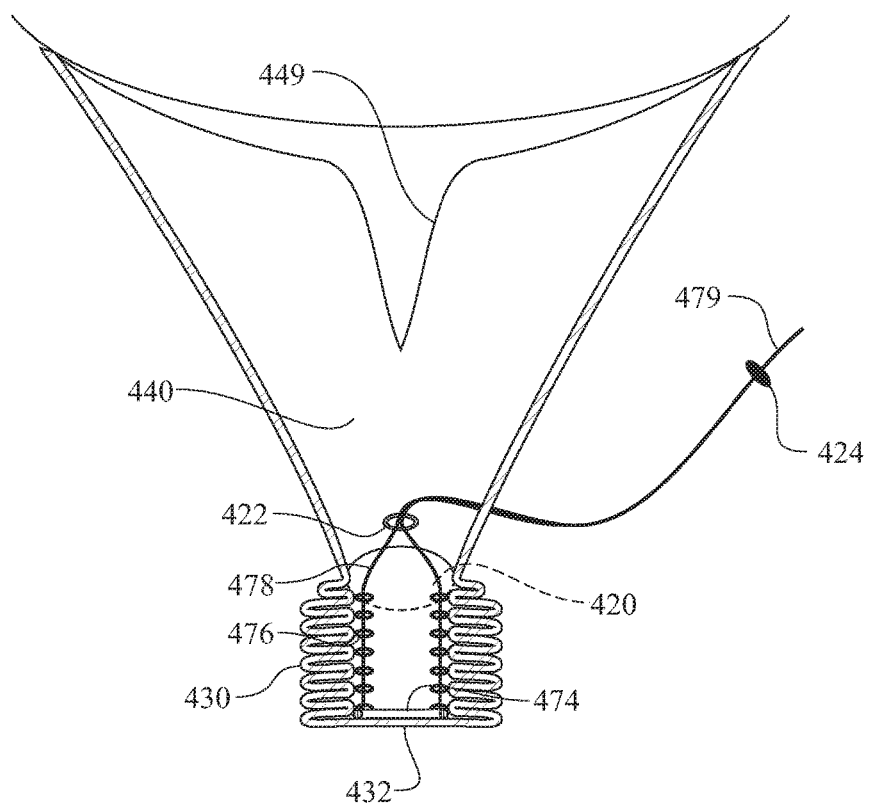
FIG. 9 presents a sectioned elevation rear view of the exemplary enhanced tubular protective sleeve originally introduced in FIG. 10, the tubular protective sleeve being shown in a contracted condition.

Upon completion of use, the medical professional can withdraw or extract the stethoscope 300 from the tubular protective sleeve 430 by gripping the grip assisting feature and applying a tensile or removal force to the stethoscope 300. Alternatively, the medical professional can grip and apply a tensile force to the draw element grip end retention element 424 or the collective draw elements 479. The tensile force would draw the tubular protective sleeve distal end panel 432 upwards, into a collapsed configuration, illustrated in FIG. 9. The gaps between adjacent draw element guide loop 476 guide an accordion style folding of the tubular protective sleeve 430, as illustrated. The draw element collection guide eyelet 422 can be located to retain the collapsed tubular protective sleeve 430 external to the broadened interior pocket 440, as shown, or located higher, drawing the collapsed tubular protective sleeve 430 into an interior of the broadened interior pocket 440.

The series of draw element guide loops 476 can be of any suitable design. The series of draw element guide loop 476 can be provided as individual loops or fabricated of a single entity. For example, the series of draw element guide loop 476 can be fabricated using an elongated flexible tubular structure, wherein sections of the tubular structure are cut out and removed to form the loops and respective gaps. In a second example, the series of draw element guide loops 476 can be formed as a single pleated tube, wherein the pleats act as an accordion.

Yet another exemplary additional feature is a clear exterior pocket 160, as shown in FIG. 1. The clear exterior pocket 160 would be fabricated of a clear or transparent material. The medical professional can place an object, such as a cellular telephone or Smartphone 199 into the clear exterior pocket 160. The clear material allows the medical professional to view the display on the cellular telephone or Smartphone 199 without contacting the device 199. The opening of the clear exterior pocket 160 can include a sealing element (not shown but well understood by those skilled in the art) to avoid contaminating the device 199 during treatment of the patient.

Figure 4:
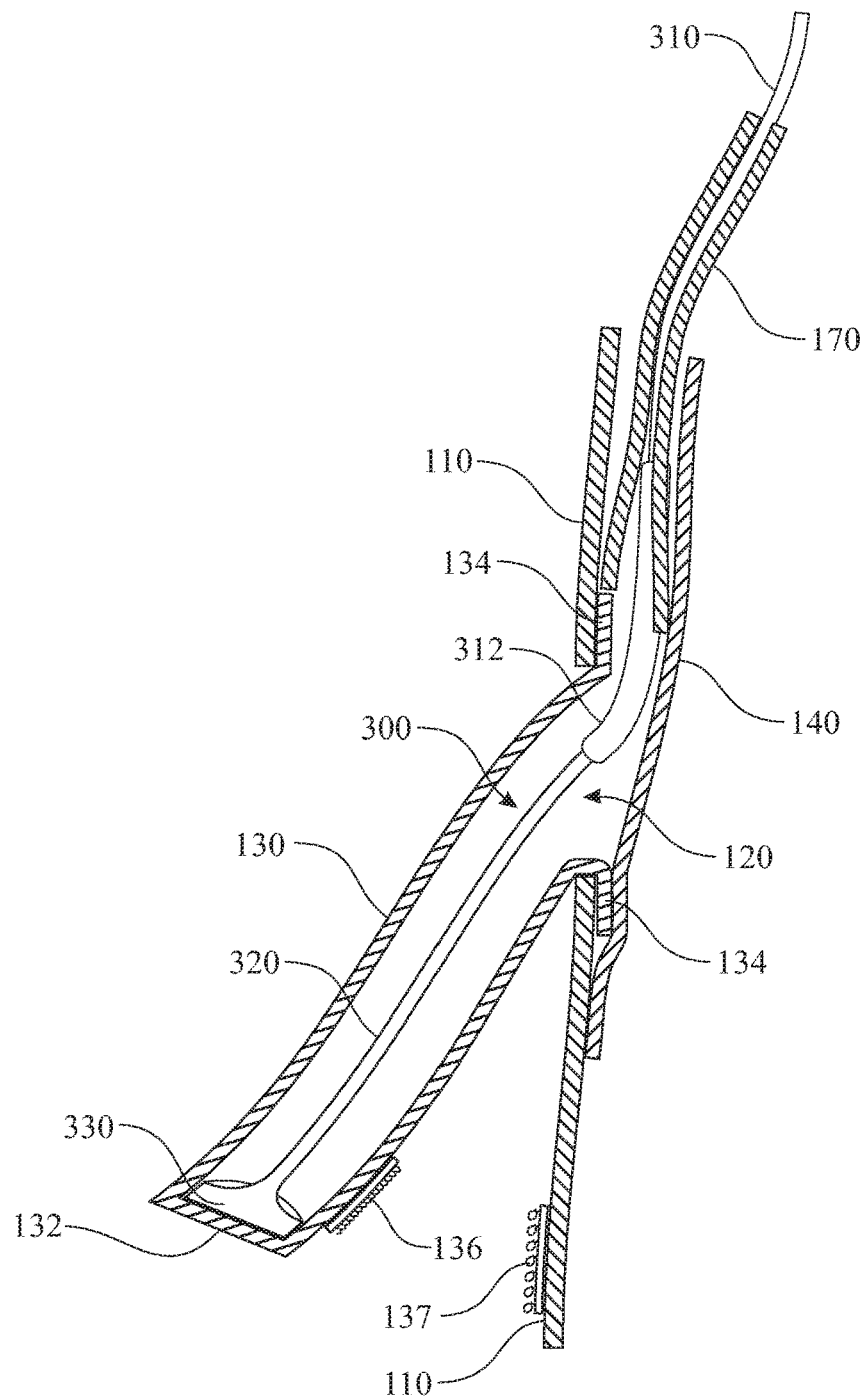
FIG. 4 presents a sectioned elevation view of the protective gown, wherein the section is taken along an elevation centerline of a tubular protective sleeve, the illustration presenting an exemplary assembly technique for assembling the tubular protective sleeve to the gown body and an exemplary use of the tubular protective sleeve.

Yet another exemplary additional feature is a tubular protective sleeve securing mechanism, such as a dense hook and loop tape section 136 and a mating dense hook and loop tape section 137 introduced in FIG. 4. The tubular protective sleeve securing mechanism can employ any suitable mechanical securing mechanism, including mating dense hook and loop tape sections 136, 137 (as shown), snaps, a tie, a ribbon, magnets, and the like. Alternatively, a pocket can be provided on an exterior of the protective gown body 110, wherein the pocket is adapted to receive and retain the tubular protective sleeve 130 therein when not in use. The mechanical securing mechanism would retain the tubular protective sleeve 130 in a position against the protective gown body 110 while not in use. The preferred tubular protective sleeve securing mechanism would enable ease of separation from the protective gown 100, thus minimizing any inhibitance during use. Although the illustrated protective gown body 110 is of a single design, it is understood that the gown body can be of any suitable design. For example, the gown body 110 can be designed as a jumpsuit, including a pair of leg coverings. The gown body 110 can include a foot covering located at a distal end of each leg covering.

It is understood that the concept can be adapted for use with other medical instruments. For example, the tubular protective sleeve can be adapted to accommodate a wireless, two unit stethoscope, such as a Bluetooth stethoscope. In a second example, the concept can be adapted to accommodate other medical equipment, such as a hand held ultrasound device. It is understood that the concept can be adapted to support and protect any other portable medical equipment and/or remote medical hand piece.

The above-described embodiments are merely exemplary illustrations of implementations set forth for a clear understanding of the principles of the invention. Many variations, combinations, modifications or equivalents may be substituted for elements thereof without departing from the scope of the invention. Therefore, it is intended that the invention not be limited to the particular embodiments disclosed as the best mode contemplated for carrying out this invention, but that the invention will include all the embodiments falling within the scope of the appended claims.

REF. NO. DESCRIPTION 100 protective gown
110 protective gown body
112 protective gown sleeve
113 gathered sleeve opening
114 glove 115 finger loop
116 protective gown neckline
118 gown body outer surface
119 gown body inner surface
120 centrally located orifice
130 tubular protective sleeve
132 tubular protective sleeve distal end panel
134 sleeve assembly flange
136 dense hook and loop tape section
137 mating dense hook and loop tape section
140 broadened interior pocket
142 "V" shaped broadened interior pocket
144 "U" shaped broadened interior pocket
146 rectangular shaped broadened interior pocket
149 broadened interior pocket stethoscope lead in
150 attached mask
152 mask and gown seam
154 mask retention strap
156 head covering
160 clear exterior pocket
170 stethoscope adjustment access pocket
172 pocket aperture
180 temporary support strap
198 glove covered hand
199 portable electronics device
200 medical professional
210 patient
212 patient's chest
300 stethoscope
310 stethoscope binaural
312 stethoscope earpiece
320 flexible tubing
322 stethoscope bisected tubing section
330 drum and diaphragm
420 centrally located orifice
422 draw element collection guide eyelet
424 draw element grip end retention element
430 tubular protective sleeve
432 tubular protective sleeve distal end panel
440 broadened interior pocket
449 broadened interior pocket stethoscope lead in
474 distal end panel support element
476 draw element guide loop
478 draw element
479 collective draw elements

What is claimed is:

1. A protective medical gown comprising:
a gown body adapted to be worn by a medical professional, the gown body having a front panel section, the gown body oriented by an exterior surface and an interior surface when worn;
an orifice centrally located in a central region of a front portion of the gown body; and
a tubular protective sleeve joined to the gown body at an attachment end circumscribing the centrally located orifice, the tubular protective sleeve extending freely and outward from the gown body, the tubular protective sleeve having a shape and size to receive a distal portion of a medical device;
an interior pocket separate segment from the tubular protective sleeve assembled to the interior surface of the gown body, the interior pocket comprising a sheet of material joined to the interior surface of the gown body along each of a first edge of the interior pocket and a second edge of the interior pocket, the interior pocket located to support a proximal portion of the medical device, having a first end proximate the centrally located orifice and a second end proximate a neckline of the gown body,
wherein the gown body and tubular protective sleeve are fabricated of a material and assembled to one another creating an impervious barrier to biomedical hazardous materials.

2. A protective medical gown as recited in claim 1, further comprising:
a first color on the exterior surface of the gown body; and
a second color on interior surface of the gown body,
wherein the first color and the second color differ from one another.

3. A protective gown as recited in claim 1, the tubular protective sleeve further comprising:
a sleeve assembly flange extending about the attachment end of the tubular protective sleeve,
wherein the sleeve assembly flange and the gown body are joined to one another creating the impervious barrier to biomedical hazardous materials.

4. A protective medical gown as recited in claim 1, further comprising:
at least one medical device adjustment access pocket located proximate a neckline of the gown body,
wherein the at least one medical device adjustment access pocket is adapted to enabled a user to adjust a position of a medical device partially inserted within the tubular protective sleeve.

5. A protective medical gown as recited in claim 1, the gown body further comprising:
a rear gown opening extending downward from a neckline, the rear gown opening defining a gown body first rear section and a gown body second rear section,
the protective medical gown further comprising a temporary support strap, the temporary support strap secured to the gown body at a position proximate the neckline on the gown body first rear section, extending across the rear gown opening, and secured to the gown body at a position proximate the neckline on the gown body second rear section,
wherein the temporary support strap and the neckline of the gown body form a gown supporting loop, wherein the gown supporting loop is adapted to be placed about a neck of a wearer to support the protective medical gown when the wearer is placing the protective medical gown on the wearer's body.

6. A protective medical gown as recited in claim 1, further comprising at least one of:
an integral glove formed at a distal end of each protective gown body sleeve of a pair of protective gown body sleeves of the gown body,
a finger loop formed proximate a distal end of each protective gown body sleeve of the pair of protective gown body sleeves of the gown body,
a gathered sleeve opening formed at a distal end of each protective gown body sleeve of the pair of protective gown body sleeves of the gown body,
a mask attached to the gown body at a location proximate a neckline of the gown body,
a partial head covering attached to the gown body at a location proximate a neckline of the gown body,
a complete head covering attached to the gown body at a location proximate a neckline of the gown body, and
an article pocket carried by the exterior surface of the gown body, the article pocket being fabricated of a transparent material.

7. A protective medical gown as recited in claim 1, further comprising:
   a sleeve contraction system,
   wherein the sleeve contraction system enables contraction of the tubular protective sleeve drawing a distal, free end of the tubular protective sleeve towards the attachment end of the protective tubular sleeve.

8. A protective medical gown as recited in claim 1, further comprising:
   a sleeve contraction system comprising:
      a series of draw element guide loops carried by the tubular protective sleeve, the draw element guide loops being configured in a generally linear, spatial arrangement, and
      at least one draw element, each draw element having a distal end assembled to the sleeve at a position proximate the tubular protective sleeve distal end panel, each draw element being routed through the draw element guide loops to a position proximate the centrally located orifice,
   wherein the sleeve contraction system enables contraction of the tubular protective sleeve drawing a distal, free end of the tubular protective sleeve towards the attachment end of the protective tubular sleeve.

9. A protective medical gown as recited in claim 1, further comprising:
   a medical device adjustment pocket comprising an enclosed pocket body having a pocket aperture, the pocket aperture being in registration with and secured about an aperture formed through the gown body, the enclosed pocket body being at least partially extending into the interior pocket, thus enabling manipulation of the medical device while the medical device adjustment pocket provides a barrier between a hand of the medical professional and the medical device.

10. A protective medical gown comprising:
    a gown body adapted to be worn by a medical professional, the gown body having a front panel section, the gown body oriented by an exterior surface and an interior surface when worn;
    an orifice centrally located in a central region of a front portion of the gown body;
    a tubular protective sleeve joined to the gown body at an attachment end circumscribing the centrally located orifice, the tubular protective sleeve extending freely and outward from the gown body, the tubular protective sleeve having a shape and size to receive a distal end of a medical device; and
    a broadened interior pocket separate segment from the tubular protective sleeve assembled to the interior surface of the gown body, the broadened interior pocket comprising a sheet of material joined to the interior surface along each of a first edge of the interior pocket and a second edge of the interior pocket, the interior pocket located to support a proximal end of the medical device, having a first, narrow end located proximate the centrally located orifice and a second, broader end, located proximate a neckline of the gown body,
    wherein the gown body and tubular protective sleeve are fabricated of a material and assembled to one another creating an impervious barrier to biomedical hazardous materials.

11. A protective medical gown as recited in claim 10, wherein a portion of the broadened interior pocket is formed having at least one of the following shapes:
    a triangular shape,
    a rectangular shape, and
    a rounded shape.

12. A protective medical gown as recited in claim 10, the broadened interior pocket further comprising a slit formed in the sheet of material, the slit extending from the broader end of the broadened interior pocket of the broadened interior pocket towards a lower edge of the broadened interior pocket.

13. A protective medical gown as recited in claim 10, wherein the tubular protective sleeve is sized and shaped to receive a flexible tubing and diaphragm of a stethoscope; and
    wherein the broadened interior pocket is sized and shaped to receive and support a stethoscope binaural of the stethoscope.

14. A protective medical gown as recited in claim 10, further comprising:
    a first color on the exterior surface of the gown body; and
    a second color on interior surface of the gown body,
    wherein the first color and the second color differ from one another.

15. A protective gown as recited in claim 10, the tubular protective sleeve further comprising:
    a sleeve assembly flange extending about the attachment end of the tubular protective sleeve,
    wherein the sleeve assembly flange and the gown body are joined to one another creating the impervious barrier to biomedical hazardous materials.

16. A protective medical gown as recited in claim 10, wherein the interior pocket and the tubular protective sleeve are sized and shaped to support and contain a stethoscope, the protective gown further comprising:
    at least one stethoscope adjustment access pocket located proximate a neckline of the gown body,
    wherein the at least one stethoscope adjustment access pocket is adapted to enabled a user to adjust a position of a medical device partially inserted within the tubular protective sleeve.

17. A protective medical gown as recited in claim 10, the gown body further comprising:
    a rear gown opening extending downward from a neckline, the rear gown opening defining a gown body first rear section and a gown body second rear section,
    the protective medical gown further comprising a temporary support strap, the temporary support strap secured to the gown body at a position proximate the neckline on the gown body first rear section, extending across the rear gown opening, and secured to the gown body at a position proximate the neckline on the gown body second rear section,
    wherein the temporary support strap and the neckline of the gown body form a gown supporting loop, wherein the gown supporting loop is adapted to be placed about a neck of a wearer to support the protective medical gown when the wearer is placing the protective medical gown on the wearer's body.

18. A protective medical gown as recited in claim 10, further comprising at least one of:
    an integral glove formed at a distal end of each protective gown body sleeve of a pair of protective gown body sleeves of the gown body,
    a finger loop formed proximate a distal end of each protective gown body sleeve of the pair of protective gown body sleeves of the gown body, a gathered sleeve opening formed at a distal end of each protective gown body sleeve of the pair of protective gown body sleeves of the gown body, a mask attached to the gown body at a location proximate a neckline of the gown body, a partial head covering attached to the gown body at a location proximate a neckline of the gown body, a complete head covering attached to the gown body at a location proximate a neckline of the gown body, and an article pocket carried by the exterior surface of the gown body, the article pocket being fabricated of a transparent material.

19. A protective medical gown as recited in claim 10, further comprising:

a sleeve contraction system, wherein the sleeve contraction system enables contraction of the tubular protective sleeve drawing a distal, free end of the tubular protective sleeve towards the attachment end of the protective tubular sleeve.

20. A protective medical gown as recited in claim 10, further comprising:

a sleeve contraction system comprising:

a series of draw element guide loops carried by the tubular protective sleeve, the draw element guide loops being configured in a generally linear, spatial arrangement, and at least one draw element, each draw element having a distal end assembled to the sleeve at a position proximate the tubular protective sleeve distal end panel, each draw element being routed through the draw element guide loops to a position proximate the centrally located orifice, wherein the sleeve contraction system enables contraction of the tubular protective sleeve drawing a distal, free end of the tubular protective sleeve towards the attachment end of the protective tubular sleeve.

21. A protective medical gown comprising:

a gown body adapted to be worn by a medical professional, the gown body having a front panel section, a first rear panel section, a second rear panel section, and a pair of sleeves, the gown body oriented by an exterior surface and an interior surface when worn;

an orifice centrally located in a central region of a front portion of the gown body;

a tubular protective sleeve joined to the gown body at an attachment end circumscribing the centrally located orifice, the tubular protective sleeve extending freely and outward from the gown body, the tubular protective sleeve having a shape and size to receive a distal portion of a medical device; and a medical device adjustment pocket separate segment from the tubular protective sleeve comprising an enclosed pocket body having a pocket aperture, the pocket aperture being in registration with and secured about an aperture formed through the gown body, the enclosed pocket body being at least partially extending into the interior pocket, thus enabling manipulation of the medical device while the medical device adjustment pocket provides a barrier between a hand of the medical professional and the medical device, wherein the gown body and tubular protective sleeve are fabricated of a material and assembled to one another creating an impervious barrier to biomedical hazardous materials.

22. A protective medical gown as recited in claim 21, wherein the tubular protective sleeve is sized and shaped to receive a flexible tubing and diaphragm of a stethoscope; and wherein the broadened interior pocket is sized and shaped to receive and support a stethoscope binaural of the stethoscope.

23. A protective medical gown as recited in claim 21, further comprising:

a first color on the exterior surface of the gown body; and a second color on interior surface of the gown body, wherein the first color and the second color differ from one another.

24. A protective gown as recited in claim 21, the tubular protective sleeve further comprising:

a sleeve assembly flange extending about the attachment end of the tubular protective sleeve, wherein the sleeve assembly flange and the gown body are joined to one another creating the impervious barrier to biomedical hazardous materials.

25. A protective medical gown as recited in claim 21, the gown body further comprising:

a rear gown opening extending downward from a neckline, the rear gown opening defining a gown body first rear section and a gown body second rear section, the protective medical gown further comprising a temporary support strap, the temporary support strap secured to the gown body at a position proximate the neckline on the gown body first rear section, extending across the rear gown opening, and secured to the gown body at a position proximate the neckline on the gown body second rear section, wherein the temporary support strap and the neckline of the gown body form a gown supporting loop, wherein the gown supporting loop is adapted to be placed about a neck of a wearer to support the protective medical gown when the wearer is placing the protective medical gown on the wearer's body.

26. A protective medical gown as recited in claim 21, further comprising:

a sleeve contraction system, wherein the sleeve contraction system enables contraction of the tubular protective sleeve drawing a distal, free end of the tubular protective sleeve towards the attachment end of the protective tubular sleeve.

27. A protective medical gown as recited in claim 21, further comprising:

a sleeve contraction system comprising:

a series of draw element guide loops carried by the tubular protective sleeve, the draw element guide loops being configured in a generally linear, spatial arrangement, and at least one draw element, each draw element having a distal end assembled to the sleeve at a position proximate the tubular protective sleeve distal end panel, each draw element being routed through the draw element guide loops to a position proximate the centrally located orifice, wherein the sleeve contraction system enables contraction of the tubular protective sleeve drawing a distal, free end of the tubular protective sleeve towards the attachment end of the protective tubular sleeve.

\* \* \* \* \*